United States Patent
Zhu et al.

(10) Patent No.: US 10,505,234 B2
(45) Date of Patent: Dec. 10, 2019

(54) BATTERY CELL AND N SITU BATTERY ELECTRODE ANALYSIS METHOD

(71) Applicant: BATTELLE MEMORIAL INSTITUTE, Richland, WA (US)

(72) Inventors: Zihua Zhu, Richland, WA (US); Chongmin Wang, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 326 days.

(21) Appl. No.: 15/240,937

(22) Filed: Aug. 18, 2016

(65) Prior Publication Data

US 2017/0047619 A1    Feb. 16, 2017

Related U.S. Application Data

(63) Continuation-in-part of application No. 15/056,880, filed on Feb. 29, 2016, which is a continuation of
(Continued)

(51) Int. Cl.
| | |
|---|---|
| *H01M 10/48* | (2006.01) |
| *H01M 10/42* | (2006.01) |
| *G01N 23/2204* | (2018.01) |
| *H01M 4/38* | (2006.01) |
| *G01N 27/447* | (2006.01) |

(52) U.S. Cl.
CPC ........ *H01M 10/48* (2013.01); *G01N 23/2204* (2013.01); *H01M 10/4285* (2013.01); *G01N 27/447* (2013.01); *H01M 4/382* (2013.01)

(58) Field of Classification Search
CPC combination set(s) only.
See application file for complete search history.

(56) References Cited

U.S. PATENT DOCUMENTS

| | | |
|---|---|---|
| 4,860,224 A | 8/1989 | Cashell et al. |
| 6,758,961 B1 | 7/2004 | Vogel et al. |
| (Continued) | | |

FOREIGN PATENT DOCUMENTS

| | | | | |
|---|---|---|---|---|
| CN | 105390762 | * | 3/2016 | ........ H01M 10/0525 |
| EP | 2075821 | | 1/2009 | |
| (Continued) | | | | |

OTHER PUBLICATIONS

Wilson, James, et al. Measurement of three-dimensional microstructure in a LiCoO2 positive electrode. Journal of Power Sources 196 (2011) 3433-3447 (Year: 2011).*
(Continued)

*Primary Examiner* — Nathaniel J Kolb
(74) *Attorney, Agent, or Firm* — Wells St. John P.S.

(57) ABSTRACT

Battery cells are provided that can include: a housing defining a chamber having a fluid inlet and outlet; an anode at one side of the housing; a cathode at another side of the housing opposing and spaced apart from the anode a sufficient amount to allow for electrolyte between the anode and cathode; and the other side of the chamber defined by an ion permeable member. Methods for in situ battery electrode analysis are provided and these methods can include: providing a battery cell having an anode and a cathode; exposing the battery cell to an ion beam while the battery cell is operational to form secondary ions; and detecting the secondary ions to analyze the battery.

9 Claims, 9 Drawing Sheets

Related U.S. Application Data application No. 14/050,144, filed on Oct. 9, 2013, now Pat. No. 9,274,059, which is a continuation-in-part of application No. 13/047,025, filed on Mar. 14, 2011, now Pat. No. 8,555,710.

(56) References Cited

U.S. PATENT DOCUMENTS

| | | | |
|---|---|---|---|
| 7,201,836 | B2 | 4/2007 | Vogel et al. |
| 7,204,139 | B2 | 4/2007 | Takayama |
| 7,244,349 | B2 | 7/2007 | Vogel et al. |
| 7,387,715 | B2 | 6/2008 | Vogel et al. |
| 7,906,760 | B2 | 3/2011 | Nishiyama et al. |
| 8,059,271 | B2 | 11/2011 | Marsh et al. |
| 8,102,523 | B1 | 1/2012 | Marsh et al. |
| 8,555,710 | B2 | 10/2013 | Yu et al. |
| 9,022,652 | B2 * | 5/2015 | Chupas ............ G01N 23/20025 378/208 |
| 9,274,059 | B2 | 3/2016 | Yu et al. |
| 9,324,539 | B2 | 4/2016 | Damiano, Jr. et al. |
| 9,594,034 | B1 | 3/2017 | Pompa |
| 2004/0046120 | A1 | 3/2004 | Moses et al. |
| 2005/0045821 | A1 * | 3/2005 | Noji ..................... G01N 23/225 250/311 |
| 2005/0233066 | A1 * | 10/2005 | Sunagawa ................ C23C 24/04 427/58 |
| 2006/0199260 | A1 | 9/2006 | Zhang et al. |
| 2007/0145287 | A1 | 6/2007 | Chao et al. |
| 2007/0231850 | A1 | 10/2007 | Geoffrey et al. |
| 2007/0267295 | A1 | 11/2007 | Chang et al. |
| 2008/0057570 | A1 | 3/2008 | Natarajan et al. |
| 2009/0166536 | A1 | 7/2009 | Suga et al. |
| 2009/0294702 | A1 | 12/2009 | Imanishi et al. |
| 2009/0323069 | A1 | 12/2009 | Naessens et al. |
| 2010/0193398 | A1 | 8/2010 | Marsh et al. |
| 2012/0017415 | A1 | 1/2012 | Marsh et al. |
| 2012/0148880 | A1 * | 6/2012 | Schaefer ........... H01M 10/4207 429/50 |
| 2012/0234082 | A1 | 9/2012 | Yu et al. |
| 2012/0298883 | A1 | 11/2012 | Grogan et al. |
| 2014/0093052 | A1 * | 4/2014 | Chupas ............ G01N 23/20025 378/208 |
| 2016/0071685 | A1 | 3/2016 | Kawanishi et al. |

FOREIGN PATENT DOCUMENTS

| | | |
|---|---|---|
| EP | 2388575 | 11/2011 |
| JP | 2002-148157 | 5/2002 |
| KR | 10-0956165 | 5/2010 |
| WO | WO 2011009209 | 1/2011 |
| WO | WO 2012125216 | 9/2012 |
| WO | WO PCT/US2012/020136 | 9/2013 |
| WO | WO 2016/088710 | 5/2018 |

OTHER PUBLICATIONS

Holtz, Megan et al. Nanoscale Imaging of Lithium Ion Distribution In Situ Operation of Battery Electrode and Electrolyte. arXiv. Nov. 2013. (Year: 2013).*
Machine translation of CN105390762 (Year: 2016).*
WO PCT/US2018/028708 Search Rept., dated Oct. 15, 2018, Battelle Memorial Institute.
WO PCT/US2018/028708 Writ. Opin., dated Oct. 15, 2018, Battelle Memorial Institute.
WO PCT/US2012/020136 Search Rept., dated Aug. 21, 2012, Battelle Memorial Institute.
WO PCT/US2012/020136 Writ. Opin., dated Aug. 21, 2012, Battelle Memorial Institute.
Balasubramanian, M., et al., In situ X-ray diffraction and X-ray absorption studies of high-rate lithium-ion batteries, Journal of Power Sources, 92, 2001, 1-8.
Bard, A. J. et al., Studies of the Liquid/Solid Interface by Scanning Tunneling Microscopy and Scanning Electrochemical Microscopy, Faraday Discuss., 94, 1992, 1-22.
Batina, N., et al., Atomic Level Characterization of the Iodine-Modified Au(111) Electrode Surface Perchloric Acid Solution by In-Situ STM and ex-Situ LEED, Langmuir, 11, 1995, 4568-4576.
Chen, A., et al., Iodide adsorption at the Au(111) electrode surface, Journal of Electroanalytical Chemistry, 467, 1999, 342-353.
Dowsett, M. G., et al., Cell for Simultaneous Synchrotron Radiation X-ray and Electrochemical Corrosion Measurements on Cultural Heritage Metals and Other Materials, Anal. Chem., 78, 2006, 3360-3365.
Foresti, M. L., et al. In situ X-ray analysis under controlled potential conditions: An Innovative step and its application to the investigaton of ultrathin films electrodeposited on Ag(111), Electrochemica Acta, 51, 2006, 5532-5539.
Gao, X. P., et al., Sensitivity of Electrochemical Adlayer Structure to the Metal Crystallographic Orientation: Potential-Dependent Iodide Adsorption on Au(100) in Comparison with Other Low-Index Surfaces, J. Phys. Chem., 98, 1994, 8086-8095.
Gu, N., et al., Simultaneous determination of both the calibration consiant in an electrochemical quartz crystal microbalance and the active surface area of a polycrystalline gold electrode, Electrochemistry Communications, 2, 2000, 45-50.
Hamelin, A., et al., Cyclic voltammetry at gold single-crystal surfaces. Part 1. Behavior at low-index faces, Journal of Electroanalytical Chemistry, 407, 1996, 1-11.
Hamelin, A., et al., Cyclic voltammetry at gold single-crystal surfaces. Part 2. Behavior at low-index faces, Journal of Electroanalytical Chemistry, 407, 1996, 13-21.
Hightower, A., et al., A study of iodine adlayers on polycrystalline gold electrodes by in situ electrochemical Rutherford backscattering (ECRBS), Electrochimica Acta, 54, 20009, 1777-1783.
Hirschberg, D., et al., Identification of Endothelial Proteins by MALDI-MS Using a Compact Disc Microfluidic System, The Protein Journal, 23, 4 2004, 263-271.
Itaya, K., et al., In Situ Scanning Tunneling Microscopy of Organic Molecules Adsorbed on Iodine-Modified Au(111), Ag(111), and Pt(111) Electrodes, Solid-Liquid Electrochemical Interfaces, Amer Chemical Soc, Washington, 665, 11997, 171-188.
Itaya, K., In Situ Scanning Tunneling Microscopy in Electrolyte Solutions, Progress in Surface Science, 58, 3, 1998, 121-248.
Lee, J., et al., Development of an Automated Digestion and Droplet Deposition Microfluidic Chip for Maldi-ToF MS, Journal of AM soc Mass Sapectrom, 19, 2008, 964-972.
Lei, H-W., et al., Electrochemical Quartz Crystal Microbalance Study of Halide Adsorption and Concomitant Change of Surface Excess of Water on Highly Ordered Au(111), Langmuir, 13, 1997, 3523-3528.
Leriche, J. B., et al., An electrochemical Cell for Operando Study of Lithium Batteries Using Synchrotron Radiation, Journal of the Electrochemical Society, 157, 5, 2010, A606-A610.
Liu, J., et al., Electrophoresis Separation in Open Microchannels, A Method for Coupling Electrophores With MALDI-MS Analytica Chemistry, 73, 2001, 2147-2151.
McDonald, J. C., et al., Poly(dimethylsiloxane) as a Material for Fabricating Microfluidic Devices, Accounts of Chemical Research, 35, 7, 2002, 491-499.
Murray, K. K., et al., Liquid Sample Introduction for Matrix-Assisted Laser Desorption Ionization, Analytical Chemistry, 65, 18, 1993, 2534-2537.
Ocko, B. M., et al., Structure and Electrocompression of Electrodeposited Iodine Monolayers on Au(111), J. Phys. Chem, 98, 1994, 897-906.
Ogaki, K., et al., In Situ Scanning Tunneling Microscopy of Underpotential and Bulk Deposition of Silver and Gold (111), Eiectrochimica Acta, 40, 10, 1995, 1249-1257.
Onnerjord, P., et al., Homogenous Sample Preparation for Automated High Throughput Analysis With Matrix-Assisted Laser Deposition/Ionisation Time-of-Flight Mass Spectrometry, Rapid Communications in Mass Spectrometry, 13, 1999, 315-322.
Orsnes, H., et al., A Rotating Ball Inlet for On-Line MALDI Mass Spectrometry, Analytical Chemistry, Jan. 1, 2000, p. 251-254, vol. 72, No. 1.

(56) References Cited

OTHER PUBLICATIONS

Preisler, J., et al., On-Line MALDI-TOF MS Using a Continuous Deposition Interface, Analytical Chemistry, 70, 24, 1998, 5278-5287.
Roberts, G. A., Reflection-mode x-ray powder diffraction cell for in situ studies of electrochemical reactions, Review of Scientific Instruments, 75, 5, 2004, 1251-1254,
Rodriguez, J. F., et al., Determination of the Surface Area of Gold Electrodes by Iodine Chemisorption, J. Electroanal. Chem., 233, 1987, 283-289
Scherb, G., et al., A novel thick-layer electrochemical cell for in situ x-ray diffraction, Review of Scientific instruments, 69, 2, 1998, 512-516.
Scherb, G. et al., In situ x-ray standing-wave analysis of electrodeposited Cu monolayers on GaAs(001), Physical Review B, 58, 16, 1998, 10800-10805.
Sherwood, P.M.A, Probing electrode surface chemical composition with core and valence band photoemission and an anaerobic cell, Colloids and Surfaces A: Physicochemical and Engineering Aspects, 134, 1998, 221-230.
Somarjai, G. A. , et al., Concepts, instruments, and model systems that enabled the rapid evolution of surface science, Surface Science, 603, 2009, 1293-1300.
Somarjai, G. A., et al., Impact of surface chemistry, PNAS, 108, 2011, 917-924.
Somarjai, G. A., Molecular level studies of solid-gas and solid-liquid interfaces, Surface Science, 335, 1995, 10-22.
Stuve, E. M., et al., Chemistry and physics of the "liquid"/solid interface: A surface science perspective, J. Vac. Sci. Technol. A, 11, 4, 1993, 2217-2224.
Stuve, E. M., et al., Relating the in-situ, ex-situ, and non-situ environments in surface electrochemistry, Surface Science, 335, 1995, 177-184.
Szakal, C., et al., Surface Sensitivity in Cluster-Ion-Induced Sputtering, Physical Review Letters, 96, 2005, 216104.
Tao, N. J., et al., In Situ Scanning Tunneling Microscopy Study of Iodine and Bromine Adsorption on Au(111) under Potential Control, J. Phys. Chem., 96, 1992, 5213-5217.

Wang, J., et al., In situ x-ray-diffraction and -reflectivity studies of the AU(111) electrolyte interface: Reconstruction and anion adsorption, Physical Review B, 46, 16, 1992, 10321-10338.
Warrens, S., et al., X-ray structural analysis of semi-conductor-electrolyte interfaces, Workd Scientific Publ Co Pte Ltd, Singapore, 2003.
Yamada, T., et al., Interfacial structure of iodine electrodeposited on Au(111): studies by LEED and in situ STM, Surface Science, 335, 1995, 204-209.
Yamada, T., et al., Structure of Electrochemically Deposited Iodine Adlayer on Au(111) Studied by Ultra-high Vacuum Instrumentation and in Situ STM, J. Phys. Chem., 99, 1995, 8817-8823.
Yang, L., et al., Making a hybrid microfluidic platform compatible for in situ imaging by vacuum-based techiques, Journal of Vacuum Science and Technology A, 29, 2011, 061101-1-061101-10.
Yang, L., et al., Performance of a microfluidic device for in situ ToF-SIMS analysis of selected organic molecules at aqueous surfacesl Analytical Methods, 5, 2013, 2515-2522.
Yang, L., et al., Probing liquid surfaces under vacuum using SEM and Tof-SIMS, Lab on a Chip, 11, 2011, 2481-2484.
Yu, X-Y., et al., Probing Aqueous Sruffaces by TOF-SIMS, Current Trends in Mass Spectrometry, 2011, 34-38.
Zhang, X., et al., On-Line Single Droplet Deposition for MALDI Mass Spectrometry, American Society for Mass Spectrometry, 15, 2004, 1471-1477.
Hua, X., et al. In situ molecular imaging of a hydrated biofilm in a microfiuidic rector by ToF-SIMS, Analyst, 139, 2014, 1609-1613.
Lui, B., et al., In situ chemical probing of the electrode-electrolyte interface by ToF-SIMS, Lab on a Chip, 14, 2014, 855-859.
Wu, F., et al., Advances in sealed liquid cells for in-situ TEM electrochemical investigation of lithium-ion battery, Nano Energy, 11, 2015, 196-210.
Yang, L., In situ SEM and ToF-SIMS analysis of IGG conjugated gold nanoperticles at aqueous surfaces, Sun Interface Anal., 46, 2014, 224-226.
Yu, X-Y., et al., Imaging liquidsusing microfluidic calls, Microfluid Nanofluid, 15, 2013, 725-744.

* cited by examiner

FIG. 9B ically and chemical stability of electrodes in the battery, minimiz-
BATTERY CELL AND N SITU BATTERY ELECTRODE ANALYSIS METHOD

CROSS REFERENCE TO RELATED APPLICATIONS

This application is a Continuation-in-Part of U.S. patent application Ser. No. 15/056,880 filed Feb. 29, 2016, which is a Continuation of U.S. patent application Ser. No. 14/050, 144 filed Oct. 9, 2013, now issued as U.S. Pat. No. 9,274, 059, which is a Continuation-in-Part of U.S. patent application Ser. No. 13/047,025 filed Mar. 14, 2011, now issued as U.S. Pat. No. 8,555,710, which references are incorporated in their entirety herein.

STATEMENT REGARDING RIGHTS TO DISCLOSURE MADE UNDER FEDERALLY-SPONSORED RESEARCH AND DEVELOPMENT

This disclosure was made with Government support under Contract DE-AC05-76RL01830 awarded by the U.S. Department of Energy. The Government has certain rights in the disclosure.

FIELD OF THE DISCLOSURE

The present disclosure relates generally to electrochemical devices and processes. More particularly, the disclosure relates to a battery cell and in situ battery electrode analysis methods.

BACKGROUND OF THE DISCLOSURE

For rechargeable batteries such as lithium (i.e., $Li^+$) ion batteries, performance and battery life depend on structural and chemical stability of electrodes in the battery, minimizing the rate of degradation of electrolytes, and controlling formation of solid electrolyte interface (SEI) layers at or on the surface of the electrodes during repeated charge-discharge cycles. However, knowledge of the dynamic structural and chemical evolution of ionic and molecular species at the electrode-liquid electrolyte interface for a rechargeable battery remains limited due to an inability to directly probe the interface during operation under reaction conditions. Because electrode surfaces are normally enclosed in a liquid electrolyte, traditional analyses of electrode surfaces require disassembling the battery and examining the electrodes and their chemical composition using imaging and spectroscopic methods ex-situ. Unfortunately, post-operation examination does not provide real-time information about molecular and ionic species that form SEI layers, structural and chemical characteristics of SEI layers during formation, or the ability to correlate real-time data to the transport of ions of interest.

For example, solvation-desolvation reactions involving active ions in electrolytes have been mostly studied using electrospray ionization (ESI) and nuclear magnetic resonance (NMR) coupled with theoretical calculations. However, ESI and NMR are bulk analysis techniques that are not effective for studying solvation-desolvation processes occurring at the electrode-electrolyte interface. Hence, formation and evolution of SEI layers during the charge and discharge cycles of Li-ion conducting batteries, as well as the associated structures and chemical species associated with the SEI layers, and an ability to correlate data from these events to the transport of the $Li^+$ ions remains elusive.

A key shortcoming of observations related to formation of SEI layers is the lack of molecular information that is spatially adjacent to the electrolyte/electrode interface. Direct molecular level observation of structural and chemical evolution of electrode surface in a rechargeable battery has not previously been possible. Lack of data in these representative areas has limited advancements in performance of rechargeable Li-ion batteries to date. Accordingly, new devices and methods are needed that provide in-situ analyses of electrodes and evolution of SEI layers at the electrode and electrode-electrolyte interface during operation rather than relying on ex-situ analyses to advance performance of rechargeable batteries. The present disclosure addresses these needs.

SUMMARY

Battery cells are provided that can include: a housing defining a chamber having a fluid inlet and outlet; an anode at one side of the housing; a cathode at another side of the housing opposing and spaced apart from the anode a sufficient amount to allow for electrolyte between the anode and cathode; and the other side of the chamber defined by an ion permeable member.

Methods for in situ battery electrode analysis are provided and these methods can include: providing a battery cell having an anode and a cathode; exposing the battery cell to an ion beam while the battery cell is operational to form secondary ions; and detecting the secondary ions to analyze the battery.

DESCRIPTION

The battery cells and methods of the present disclosure are provided with reference to FIGS. 1-9B. Generally, the present disclosure includes a rechargeable battery testing device that enables direct probing and characterization of ionic and molecular species at the electrode surface and at the solid electrode-electrolyte interface during operation (i.e., charge-discharge) of the battery. The present disclosure modifies a microfluidic device for electrochemical analysis of fluids detailed, e.g., in U.S. patent application Ser. No. 14/050,144 filed Oct. 9, 2013, now issued as U.S. Pat. No. 9,274,059 which is herein incorporated by reference in its entirety herein. Also incorporated by reference herein is the entirety of *In Situ Mass Spectrometric Determination of Molecular Structural Evolution at the Solid Electrolyte interphase in Lithium-ion batteries* by Zihua Zhu et al appearing in Nano Lett. 2015 pgs. 6170-6176.

Figure 1:
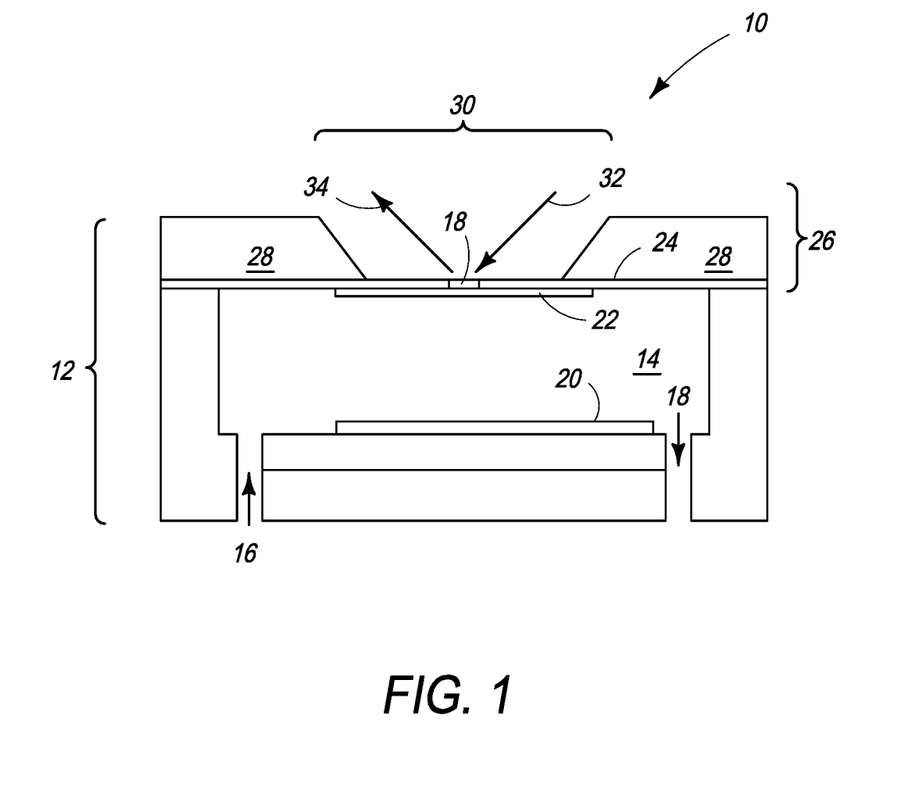
FIG. 1 illustrates one embodiment of a battery cell of the present disclosure.

Referring to FIG. 1, a battery cell 10 is shown that includes a housing 12. Housing 12 can be constructed of PEEK® material, for example, and can be constructed of multiple components, including a frame component to be described later. Inlets and outlets to chamber 14 can be within housing 12. These inlets and outlets are shown as 16 and 18, respectively. On opposing sides of chamber 14 can be cathode 20 and anode 22. Cathode 20 can be associated with a sidewall housing 12 and anode 22 can be associated with an opposing sidewall of housing 12. Between cathode 20 and anode 22 can be space within chamber 14 to allow for electrolyte solution to exist therebetween. This electrolyte solution can be provided through the inlets and outlets 16 and 18, respectively. Along at least one sidewall of housing 12 can be ion permeable member 24. Ion permeable member 24 can have a construction described herein, and this ion permeable member can form a portion of a frame 26, which includes ion permeable member 24, cathode 22 as well as frame 28. Frame 28 can be constructed of Si. In accordance with example implementations, frame 28 can have a beveled edge providing an opening to expose ion permeable member 24. In accordance with example implementations, secondary ion mass spectrometry (SIMS) can be performed in a small opening 18 (~2 microns diameter) located at the center of ion permeable member 24. Primary ions 32 can be provided to this opening, and secondary ions can be collected for detection at 34. In accordance with example implementations, this SIMS analysis and detection is provided at 30.

Figure 2A:
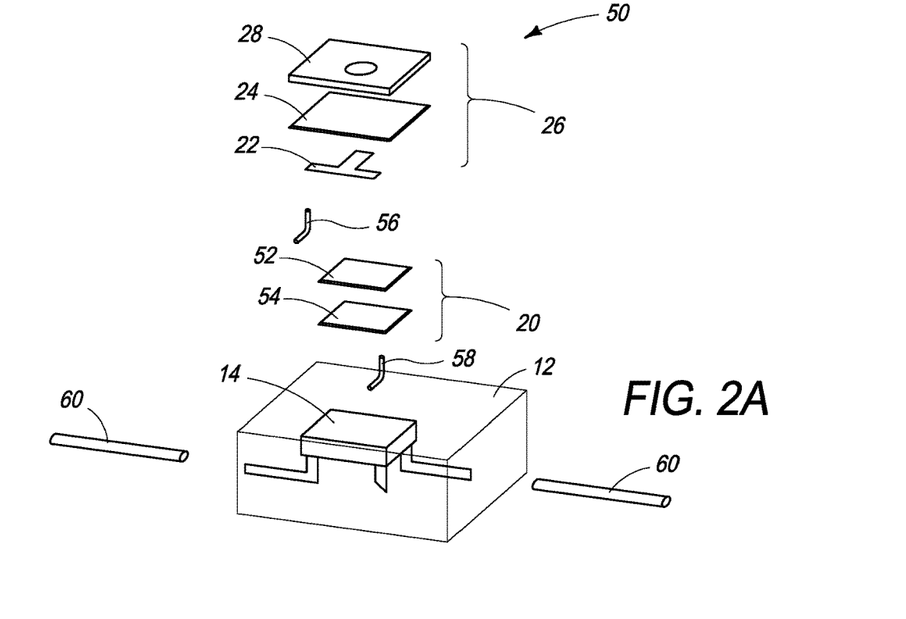
FIGS. 2A-2C show a series of battery cell intermediates formed during an example battery cell fabrication method according to an embodiment of the disclosure.
Figure 2B:
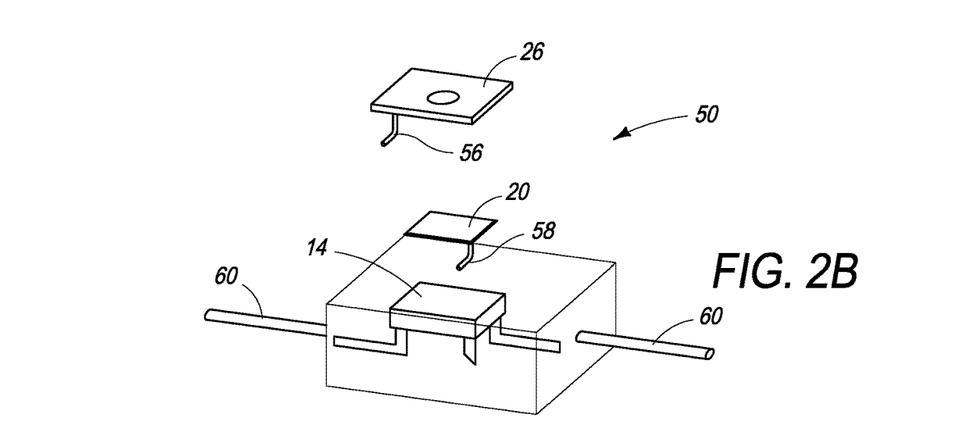
Figure 2C:
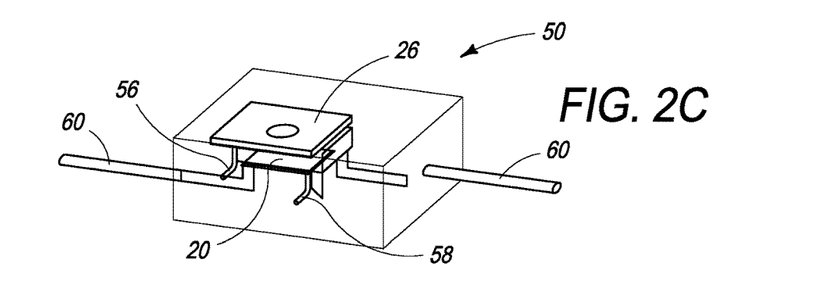

Referring next to FIGS. 2A-2C, an exemplary exploded view of one embodiment of battery cell 50 is shown. Referring first to FIG. 2A, housing 12 can be formed within a block of material such as PEEK® material, and extending and defined within housing 12 can be a chamber 14. In accordance with an example implementation, a cathode can be constructed of two components, 52 and 54, wherein 54 is an example aluminum foil component and 52 is a lithium cobalt oxide component. The lithium cobalt oxide component can be physically coated on the aluminum foil 54 to form cathode 20. In accordance with another example implementation, frame 26 can be constructed of a frame support 28, an ion permeable member 24, and an anode 22. In accordance with example implementations, the frame 28 can be a silica frame. Ion permeable member 24 can be a silicon nitride ($Si_3N_4$) membrane, and anode 22 can be a copper film. In accordance with example implementations and with reference to FIG. 2B, the anode 22 can have an electrical coupling 56 and cathode 20 can have an electrical coupling 58. Openings for these couplings can be formed within housing 12, and fluid conduits 60 can be provided to within housing 12 as well. Referring next to FIG. 2C, frame 26 can be aligned as one sidewall of chamber 14, and opposing frame 26 within housing 12. Across from chamber 14 is cathode 20. Electrolyte fluid can be provided via conduit 60 to flow between frame 26 and anode 20.

Figure 3:
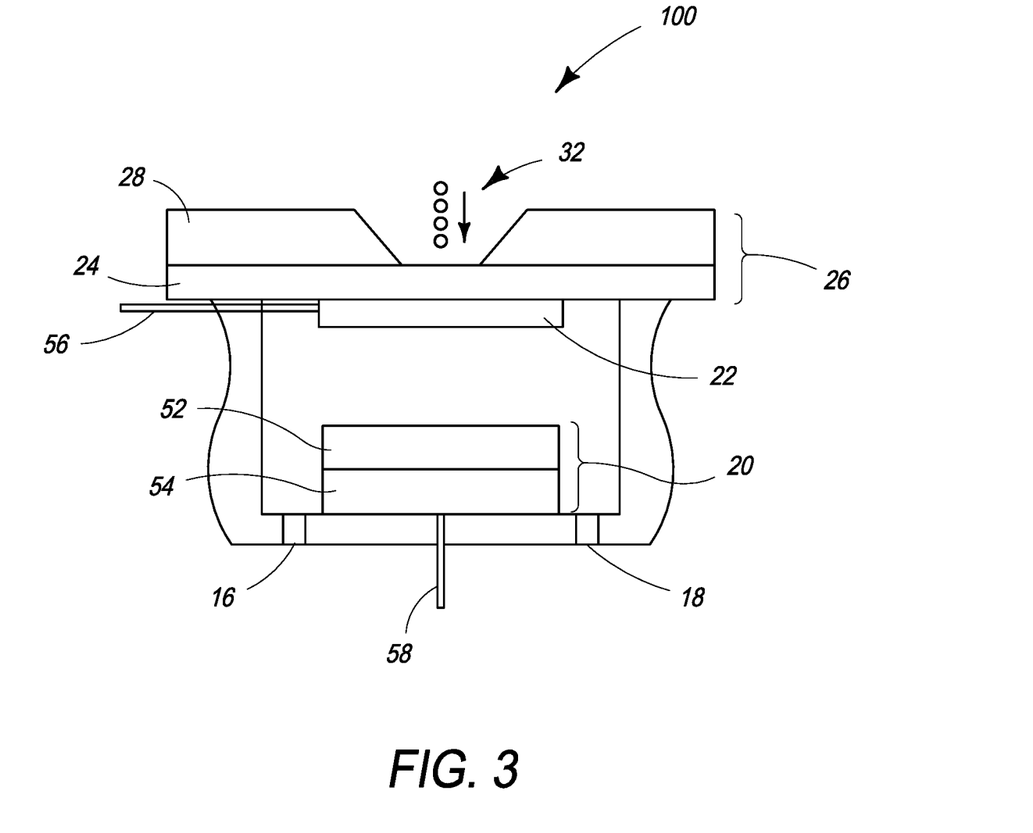
FIG. 3 is an example battery cell having an ion beam applied thereto according to an embodiment of the disclosure.

Referring next to FIG. 3, an example implementation of a battery cell 100 is provided showing frame component 26 that includes frame member 28 that can include a silicon frame at about 200 µm of thickness, a silicon nitride ion permeable member 24 that can be approximately 100 nm in thickness, and anode 22 constructed of copper that can be approximately 70 nm in thickness. Within chamber 14 can be an electrolyte solution provided through inlets and outlets 16 and 18. This electrolyte solution can be a $LiPF_6$ in organic solvent. An example organic solvent can be 1:2 (v/v) ethylene carbonate:dimethyl carbonate (EC:DMC). Cell 100 can further include cathode construction 20 that includes a lithium cobalt oxide layer over an aluminum foil layer, with the aluminum foil layer being approximately 20 µm in thickness.

In some embodiments, the battery cell can be positioned on a substrate such as glass or a silicon nitride membrane attached on a silicon frame. Electrodes in the battery testing device may be in the form of wires, thin films (e.g., sputter-deposited thin films) and suitable dimensioned forms.

The separation space between the electrodes fills with liquid electrolyte when the liquid electrolyte is introduced to the chamber. Electrolyte transports conducting ions between the anode and the cathode in the chamber.

The disclosure provides methods for fabrication of the battery cell. The methods can include multiple steps that are described herein.

The housing can be machined from a block, for example a polymeric material such as an epoxy block. The block can be a thermoplastic polymer such as polyetherimide (PEI) polymer sold commercially under the tradename ULTEM® or PEEK® or another high-performance polymer such as a semi-transparent polymer. The polymer can be an inexpensive or low-cost material that allows for low-cost fabrication and replacement. In one embodiment, the initial block can be 50.0 mm×40.0 mm×6.0 mm. In another embodiment, the block may include dimensions of 30.0 mm×10.0 mm×6.0 mm (L×W×H).

A battery chamber can be machined within the block. In one embodiment, dimensions of the chamber can be 6.5 mm×6.5 mm×1.0 mm (L×W×D). Size can be selected to be consistent with the size of the metal-coated SiN membrane assembly 26, which size is 7.5 mm×7.5 mm×0.2 mm (L×W×H) with the SiN window (0.5 mm×0.5 mm) positioned at the center of the Si frame.

The length and width of the battery chamber can be changed according to the size of anode assembly 26. For example, a size of 3.5 mm×3.5 mm (L×W) can be selected when a 5.0 mm×5.0 mm×0.2 mm (L×W×H) SiN membrane assembly 26 is used. In addition, the depth of the chamber is also variable, allowing changing of distance between anode and cathode.

Openings can be provided into the chambers that can be configured to receive tubing that introduces the liquid electrolyte and metallic wiring to each of the chamber electrodes. These openings can have a diameter of 1/32 or 1/16 inches for example. In one embodiment, tubing for the liquid electrolyte is constructed of PEEK® with a diameter of 1/32 inches. The tubing and copper wires can be placed in the openings and received within the chamber.

The cell can include at least two electrodes in the chamber, an anode and a cathode, constructed of various or selected metals including, e.g., aluminum (Al), gold (Au), platinum (Pt), Li metal, tin (Sn) and copper (Cu); metal oxides including, e.g., CuO, CoO, $LiCoO_2$, $LiFePO_4$, and $V_2O_5$; carbon (C) such as graphene, and silicon (Si). The cell can be configured without a reference electrode.

Anodes may be constructed of, or include, metals, metal oxides, carbon, graphene, silicon or other suitable electrode materials including combinations of these various materials. According to one embodiment, a metal thin film (~70 nm thick) can be deposited onto a 100 nm thick SiN film to form the anode. The metal thin film may include, but is not limited to Cu and/or Pt. Exemplary dimensions of the metal film are 1.5 mm×1.5 mm×70 nm. Exemplary dimensions of the SiN membrane are 7.5 mm×7.5 mm.

The cathode can include a thin film of active materials deposited on a metal conductive substrate. For example, the cathode can be constructed on a $LiCoO_2$ film of deposited on an Al substrate with lateral dimensions of 3.0 mm×3.0 mm.

The cell preparation method can include attaching a conducting metal wire made of copper or another conducting metal at the top of the battery chamber and securing same thereto using a conductive epoxy. The copper wire may be connected to the internal electrode through a prefabricated hole.

In the exemplary embodiment, the cathode can be constructed of a $LiCoO_2$ film coated on aluminum (Al) metal foil. The aluminum foil coated with a $LiCoO_2$ (thin film) can be associated with another wall of the battery chamber 14 to form a second electrode (cathode).

Tubes may be secured in the battery chamber after insertion into the entry holes on the battery chamber with a non-conductive epoxy.

The frame 26 can be sealed to the block to complete the housing using an epoxy resin.

The battery cell can be filled with liquid electrolyte in an argon-filled glove box using a syringe. The electrolyte of 1.0 M $LiPF_6$ in 1:2 (v/v) ethylene carbonate:dimethyl carbonate ($LiPF_6$ in EC:DMC) can be provided through the tubes and into the chamber between the electrodes. Following assembly of the cell, liquid electrolyte is sealed at the ends of the fill-tubes in the glovebox filled with argon.

The battery testing cell can be configured to allow for analysis and characterization of SEI layers when formed at the electrode surface or at the electrode-electrolyte interface in-situ during operation of the battery testing device. In-situ=a "space zone" measurement in which data is collected from inside the battery device. The term does not equate with real time (time zone). The term encompasses collection of data in-situ (i.e., internal to the battery device) and in-operando (during operation). Data analysis is performed at a later time. However, the term does not exclude analysis of data during operation or during data collection. No limitations are intended.

The cell can be placed on a SIMS stage for bombardment with primary ions and detection of secondary ions and subsequent mass spectrometry.

In some embodiments, vacuum pressure in the vacuum chamber during measurements was $2.0 \times 10^{-7}$ Torr to $5.5 \times 10^{-7}$ Torr.

Surface-sensitive analytical instruments suitable for use with the present disclosure include, for example, X-ray photoelectron spectroscopy (XPS); scanning electron microscopy (SEM); FIB/SEM; transmission electron microscopy (TEM); time-of-flight secondary ion mass spectrometer (ToF-SIMS); helium ion microscopy (HeIM); Auger electron spectroscopy (AES); and Rutherford backscattering spectrometry (RBS).

Probe beams from these various analytical instruments may be delivered through the SiN window into the battery chamber (that is under vacuum), which exposes liquid electrolytes to the probe beams and provides chemical analysis of ionic and molecular species at the surface of the electrodes, and at the electrode-electrolyte interface. Probe beams may be delivered into the liquid electrolyte at selected depths, and at selected locations of the electrodes, and at electrode-electrolyte interface.

In various embodiments, probe beams from selected analytical instrument(s) may be delivered to selected depths in the battery chamber 14 to interrogate or probe liquid electrolytes, electrode-electrolyte interfaces, and electrodes therein.

In an exemplary embodiment, for example, probe beams from the ToF-SIMS instrument may interrogate liquid electrolytes, electrode-electrolyte interfaces, and electrodes to a depth of from a few nm to hundreds of nm. However, no depth limitations are intended by the exemplary instrument.

In an exemplary embodiment, the cell enables the structure of the dual electrodes to be characterized in-situ using probe beams delivered from a combined Scanning Electron Microscope (SEM) and Focused Ion Beam (FIB) instrument.

In some applications, depth of probe beams may be selected that permit selected regions or layers of the electrode/liquid sample interface to be probed. For example, at selected depths, adsorbed molecules, SEI layers (e.g., 2 nm to 20 nm), diffuse-layers (1 nm to 1 µm), and/or modified films (e.g., 1 nm to 1 µm) may be investigated. In the instant embodiment, the liquid electrolyte to be analyzed is exposed by introducing a primary probe beam into the electrolyte to interact with the electrolyte.

In some embodiments, the device enables characterization of the structure of the electrodes in operando using a combined Scanning Electron Microscope (SEM) and a Focused Ion Beam (FIB) instrument in-situ.

The present disclosure also includes a process for direct study of the chemical composition of SEI layers that form at the electrode surface or electrode-electrolyte interface of rechargeable batteries in-situ. The method includes examining the rechargeable battery device in operando under high vacuum in the high vacuum chamber of a Time of Flight Secondary Ion Mass Spectrometer during the charge-discharge cycles of the battery.

The cell is a new miniature battery cell that can provide direct probing and analysis of the structure and chemical components at the electrode surface or electrode-electrolyte layer in-situ under battery charge and discharge conditions in-situ that enables direct analysis of the electrode-electrolyte interface during dynamic operation of a rechargeable battery, such as lithium ion battery.

In-situ liquid secondary ion mass spectroscopy (SIMS) is performed for the first time to directly observe the molecular structural evolution at the solid-liquid electrolyte interface for a lithium (Li)-ion battery under dynamic operating conditions.

The cell and methods provide in-situ, or more precisely, in operando, SIMS study of the interface between the liquid electrolyte and the lithium metal (anode) electrode. The device can also be used for in-situ SEM/FIB study of the structure of the electrodes and formation and evolution of SEI layers during operation.

The present disclosure provides characterization data regarding the evolution of ionic and molecular species as well as the chemical composition of SEI layers in ion-conducting batteries as they evolve at the electrode-electrolyte interface in-situ during charging and discharging cycles of the battery cell as a function of time. As an example, SEI layers may be probed and chemically characterized in-operando in concert with secondary ion mass spectrometry (SIMS) in-situ.

The cell can be charged and discharged in the vacuum chamber of the SIMS instrument under a constant current during SIMS analysis to study the chemical composition of the Cu/Li metal electrode by SIMS. The methods can include chemical imaging the electrode "structure" and "SEI layers" and other solid-liquid interfaces.

The Chemical imaging (as quantitative-chemical mapping) can provide the analytical capability to create a visual image of the distribution of components in the probe area from simultaneous measurement of spectra and spatial, time information.

Molecular and ionic species of interest at the SEI can be imaged including, for example, salts derived from the battery electrolyte, desolvation compounds, chemical species at the electrode-electrolyte interface that shows the evolution of the SEI layer over time, or changes to the electrode structure over time.

Further details of the process for chemical imaging is described, for example, by Zhu et al. ("In-Situ Mass Spectrometric Determination of Molecular Structural Evolution at the Solid Electrolyte Interphase in Lithium-Ion Batteries", *Nano Lett.* 2015, 15, 6170-6176) incorporated in its entirety herein by reference.

In an exemplary embodiment, the cell can be configured as a lithium-ion battery cell that can have the interface between the liquid electrolyte and the lithium metal electrode to be characterized in operando using in-situ secondary ion mass spectrometry (SIMS).

Results show that deposition of Li metal on the copper electrode leads to condensation of solvent molecules around the electrode. Chemically, this layer of solvent condensate tends to be depleted of the salt anions and with reduced concentration of $Li^+$ ions, essentially leading to the formation of a lean electrolyte layer adjacent to the electrode that contribute to over-potential of the cell. This observation alone provides unprecedented molecular level dynamic information on initial formation of a solid electrolyte interphase (SEI) layer.

$Li^+$ ions in the electrolyte are usually solvated. Upon entering the electrode, the solvated ions will be desolvated, leading to the accumulation of desolvation sheath components on or at the electrode. These accumulated components contribute to the formation of the SEI layers. Formation of the SEI layer affects transport of $Li^+$ ions through the electrolyte and degrades performance of the battery over time.

Figure 4:
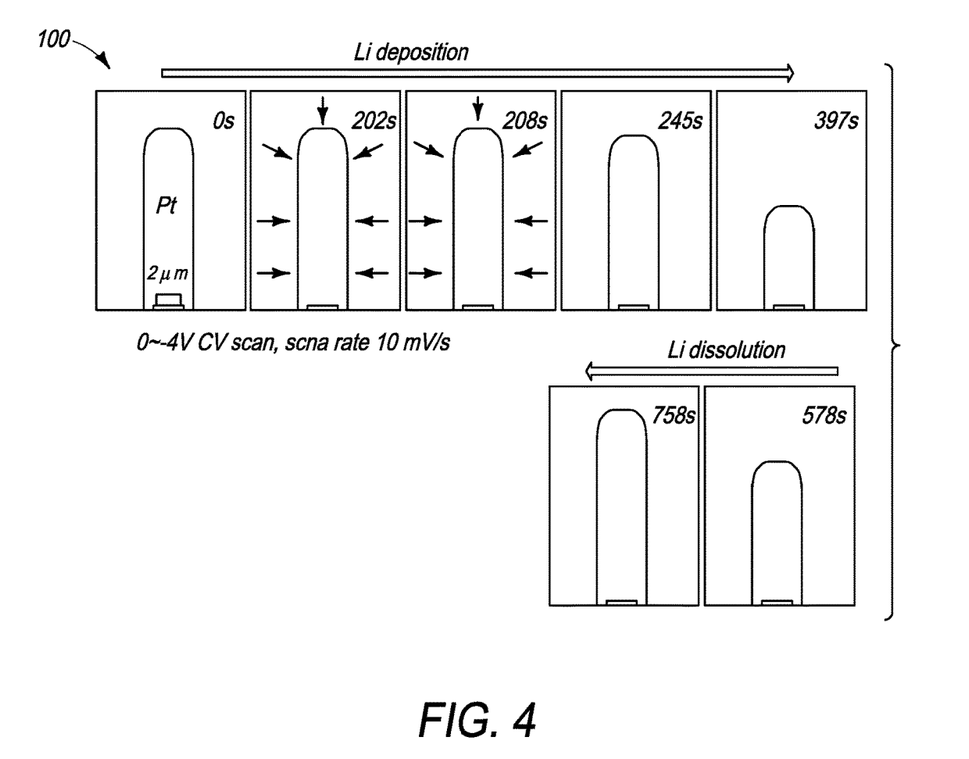
FIG. 4 is a series of in situ transmission electron microscope (TEM) images, providing morphorlogy information of the formation of SEI layer during a cyclic voltammetric scan at the surface of a platinum anode.

Referring next to FIG. 4, STEM high-angle annular dark field (HAADF) images of Li deposition and dissolution at the interface between the Pt working electrode and the $LiPF_6$/PC electrolyte during the charge discharge cycles using in situ liquid cell TEM. The formation of the SEI layer is indicated by the arrows in the second frame.

Figure 5A:
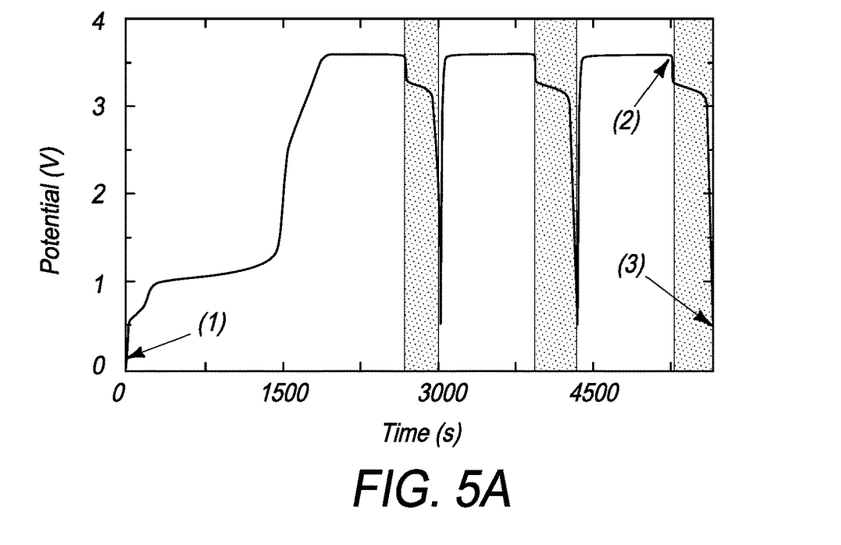
FIGS. 5A-5C provide a depiction of a typical galvanostic charge and discharge curve of a cell; a positive ion mass spectrum and two representative ion images, the third being an overlay of the previous two.
Figure 5B:
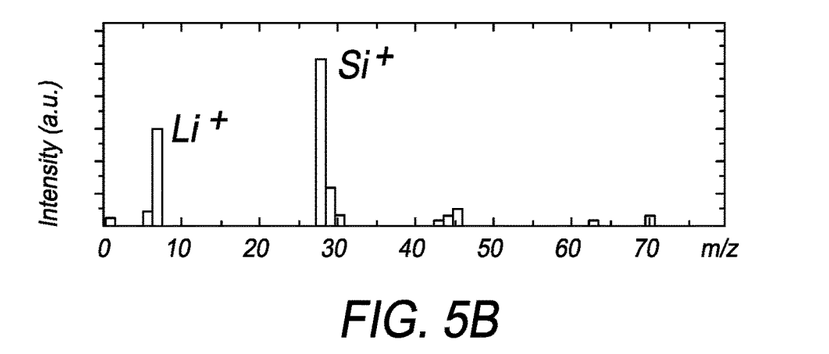
Figure 5C:
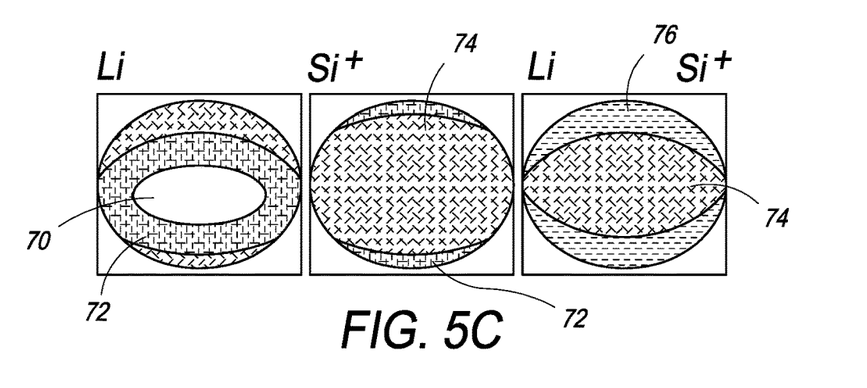

Referring next to FIG. 5A, a typical galvanostatic charge and discharge curve of an example battery cell is shown. The charging regions are left blank while the discharging regions are speckled. SIMS data are collected at (1) fresh cell, (2) after the third charging, and (3) after the third discharging. In FIGS. 5B and 5C, a typical positive ion mass spectrum and two ion images ($Li^+$ and $Si^+$) are shown (these are typically provided in color; (//////, orange, 74), (- - - -, green, 76), (blank, white, 70), and (####, yellow, 72).

Figure 6:
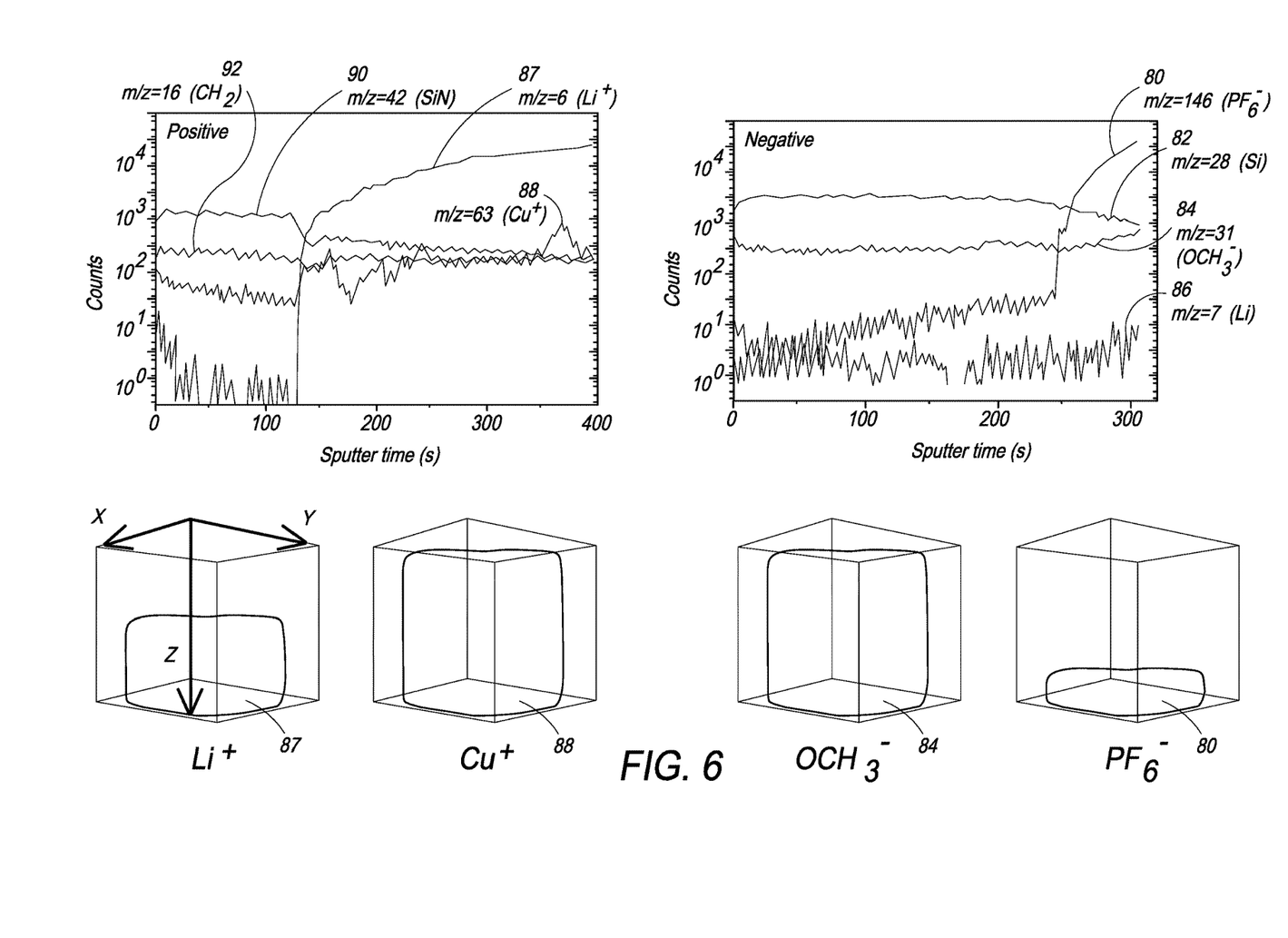
FIG. 6 depicts ToF-SIMS depth profiles of 8 representative ions collected from a fresh cell.
Figure 7:
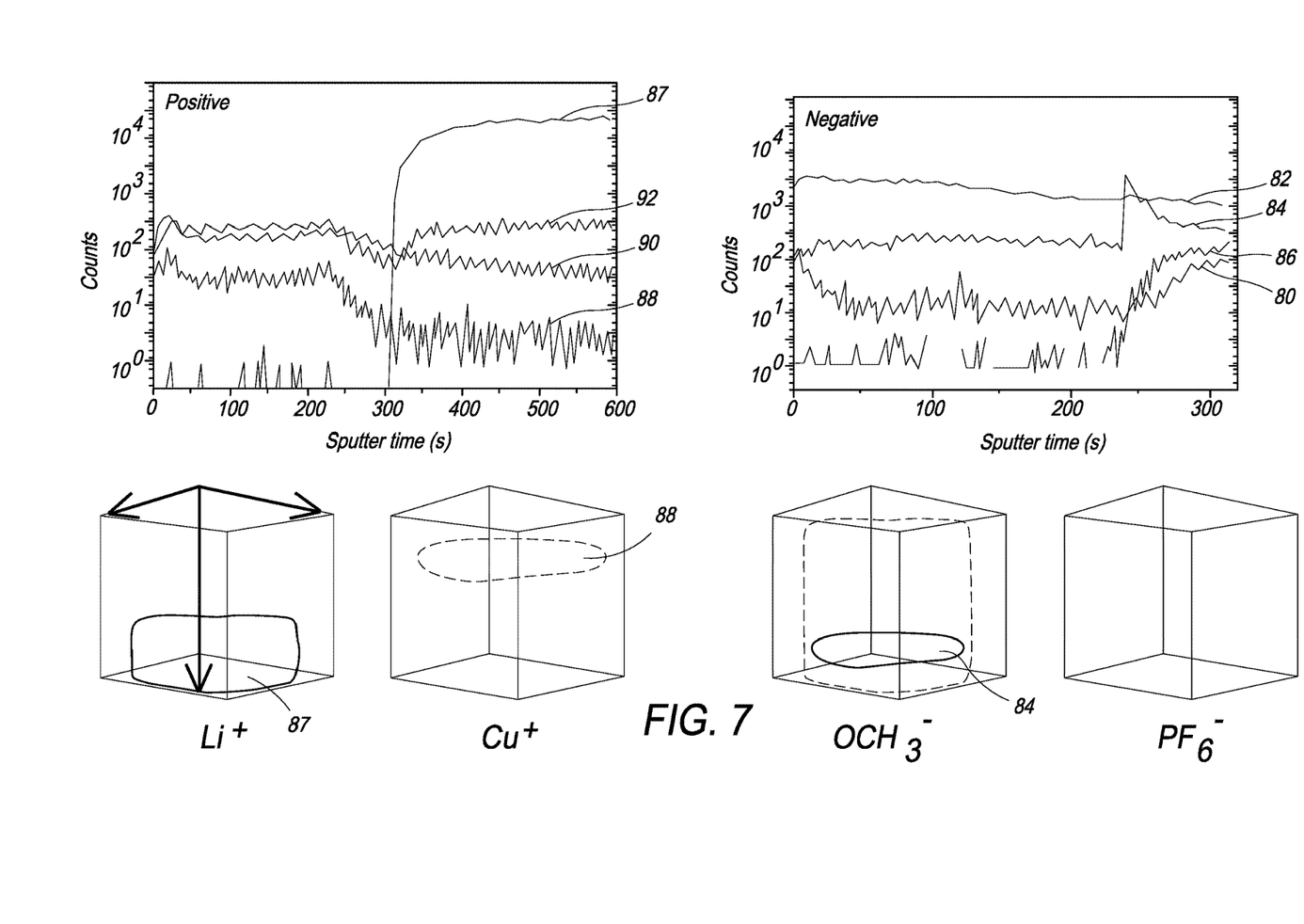
FIG. 7 depicts ToF-SIMS depth profiles of 8 representative ions collected from a cell charged to 3.6 V.
Figure 8:
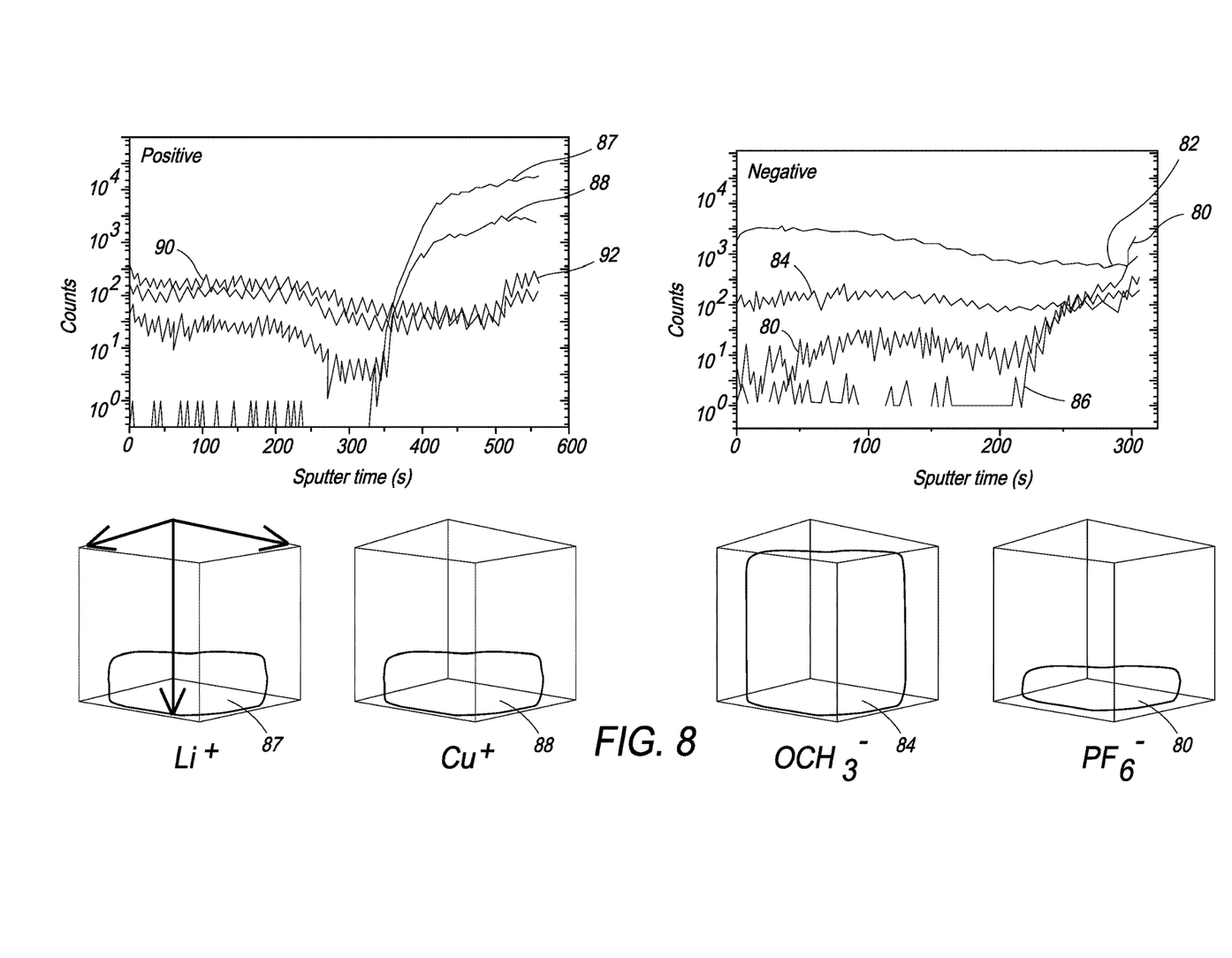
FIG. 8 depicts ToF-SIMS depth profiles of 8 representative ions collected from a cell discharged to 0.5 V.

Referring next to FIGS. 6-8, ToF-SIMS depth profiling and the re-constructed 3-dimensional configuration of several representative positive and negative secondary ions at the vicinity of the anode surface before and after charging/discharging of the battery cell are shown. (m/z=146, $PF_6^-$, 80), (m/z=28, $Si^-$, 82), (m/z=31, $OCH_3^-$, 84), (m/z=7, $Li^-$, 86), (m/z=6, $^6Li^+$, 87), (m/z=63, $Cu^+$, 88), (m/z=42, $SiN^+$, 90), (m/z=15, $CH_3^+$, 92), Depth profiles of eight representative secondary ions (four positive ions and four negative ions) before charge and discharge cycle of the battery are shown in FIG. 6. Molecular information captured at this stage (the fresh battery cell) essentially reflects structural modifications of the electrode surface as a consequence of the static interaction between the electrolyte and the electrode.

Due to the porous granular structure of the deposited copper (Cu) film, $Li^+$ and $PF_6^-$ signals were detected immediately following the $Si_3N_4$ film was sputtered through, indicating that the electrolyte with the ionized species can permeate to the $Si_3N_4$/Cu interface. In addition, $Cu^+$ signals can be observed after sputtering through the $Si_3N_4$ film. However, we noticed that although the $Si_3N_4$/Cu interface can be exposed and readily identified, it is very hard to sputter through the Cu layer even for more than 800 s sputtering. In contrast, for a control experiment of sputtering of a 70 nm thick Cu film on a $Si_3N_4$ film (without electrolyte), it took only ~40 s to penetrate the Cu film. As demonstrated in a later stage, the use of porous Cu film actually offers the advantage of allowing the detection of electrode surface reactions.

Identification of ion species and understanding the depth profiles from the solvent species at this initial stage is of interest as it provides the baseline for comparing the species observed after charge and discharge of the battery. Significant identifiable ion species include $H^+$, $C^+$, $CH^+$, $CH_2^+$, $CH_3^+$, $OCH_3^+$, $H^-$, $C^-$, $CH^-$, $C_2^-$, $C_2H^-$, and $OCH_3^-$, with many other minor peaks. For the reader's convenience, the $CH_3^+$ and $OCH_3^-$ are used as two representative ions in FIGS. 6-8. These species show a significant background in the $Si_3N_4$ film and a mild and slow increase after sputtering through the $Si_3N_4$ film, which is quite different from the jumping up behavior of the $Li^+$ and $PF_6^-$ signals. The high background of these signals may attribute to the relatively high pressure (~$1.5 \times 10^{-6}$ mbar) of residual gases in the analysis chamber. It is reasonable to expect more of a jump behavior when the $Si_3N_4$ is penetrated for these solvent-related ion species if the pressure in the analysis chamber can be significantly reduced (e.g., <$1 \times 10^{-8}$ mbar).

Upon charging the battery to 3.6 V, the depth profiles of the eight representative secondary ions are shown in FIG. 7 (the galvanostatic charge curve is shown as FIG. 5A). As compared with the fresh cell, four features were typically observed for the charged sample:

(1) Following the charging, the $Li^+$ signal shows a steeper increase upon sputtering through of the $Si_3N_4$ film, likely indicating the deposition of Li metal on the Cu electrode surface, which is morphologically very well illustrated by the recent in situ TEM observations. Consistent with the argument of the deposition of Li metal on the Cu electrode is the observation of a decrease of the $Cu^+$ signal when compared to the data before charging.

(2) There is a dramatic relative decrease of the $PF_6^-$ signal as compared with the case of the fresh sample, indicating that during the charging of the battery $PF_6^-$ ions migrate toward the cathode direction and leading to the significantly decreased concentration of $PF_6^-$ at the vicinity of the anode.

(3) Interestingly, following the charging, the solvent signals from negative ion depth profiles (e.g., $H^-$, $C^-$, $CH^-$, $C_2^-$, $C_2H^-$, $OCH_3^-$; with $OCH_3^-$ used as a representative in FIG. 7) show an immediate jump after sputtering through the $Si_3N_4$ film and gradually decrease with time with the balance signal intensity being still higher than that in the $Si_3N_4$ film. The $Li^-$ signal can be detected, and it does not show an immediate jump as soon as the sputtering through of the $Si_3N_4$ film occurs.

(4) Based on charge calculation, it is estimated that for each charging the Li deposited on the Cu electrode is ~50 nm in thickness. However, it is very difficult to sputter through the Li layer to reach the Cu layer even after long-time sputtering. These observations are all consistent with the formation of a solvent-enriched layer between the $Si_3N_4$ film and the Li/Cu electrode. This point is further consistently supported by the observation following the discharging of the battery as described in the subsequent section.

After discharging the battery, the SIMS depth profiles are shown in FIG. 8. As compared with the case of the charged state of the battery, following the discharging, the $Li^+$ signal only decreases slightly, and correspondingly, the $PF_6^-$ signal only shows a moderate increase. These observations clearly indicate that, upon the discharging of the battery, the deposited Li metal layer is not fully reversibly stripped off, suggesting formation of a dead Li layer. At the same time, the $PF_6^-$ anions are not totally recovered to the case of before charging. These observations are consistent with the direct in situ TEM observation of the nonreversible stripping of Li metal from the Cu electrode upon discharging. The formation of non-reversible Li species is also supported by the behaviors of the Cu signals. Following the discharging, the $Cu^+$ signal increases dramatically. At the same time, the Cu layer can be sputtered through as demonstrated by a dramatic increase of solvent-related signals at the end stage of depth profiles (as shown in FIG. 8, >510 s for positive secondary ion depth profiles, or >335 s for negative secondary ion depth profiles). Collectively these observations can be explained by the postulation that, after discharging, most of the channels in the porous Cu film are filled or covered by the dead Li species, blocking or inhibiting the liquid to reach the $Si_3N_4$/electrode interface. This explanation is supported by the cyclic galvanostatic charge/discharge curves shown in FIG. 5A, where the charging time is much longer than the discharging time for each charging/discharging cycle. Since a constant current was used during the charge/discharge, a shorter discharging time than that of charging indicates either certain fraction of $Li^+$ reacts with solvent to form insoluble Li salts or the covering up of the formed Li metal by the insoluble Li salts. The nonreversible Li species is essentially part of the SEI layer, which is apparently thickening with each cyclic progression of charging and discharging the battery, contributing to depletion of active Li in the battery system and therefore leading to the capacity fading and eventual failure of the battery.

Figure 9A:
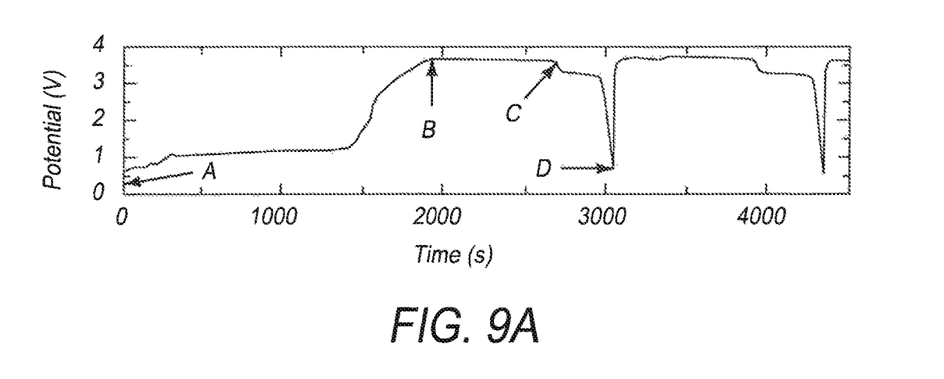
FIGS. 9A-9B depict a schematic illustration showing the molecular level stripping and clustering at the Cu anode-electrolyte interface during the charge and discharge of a Li-ion battery cell.
Figure 9B:
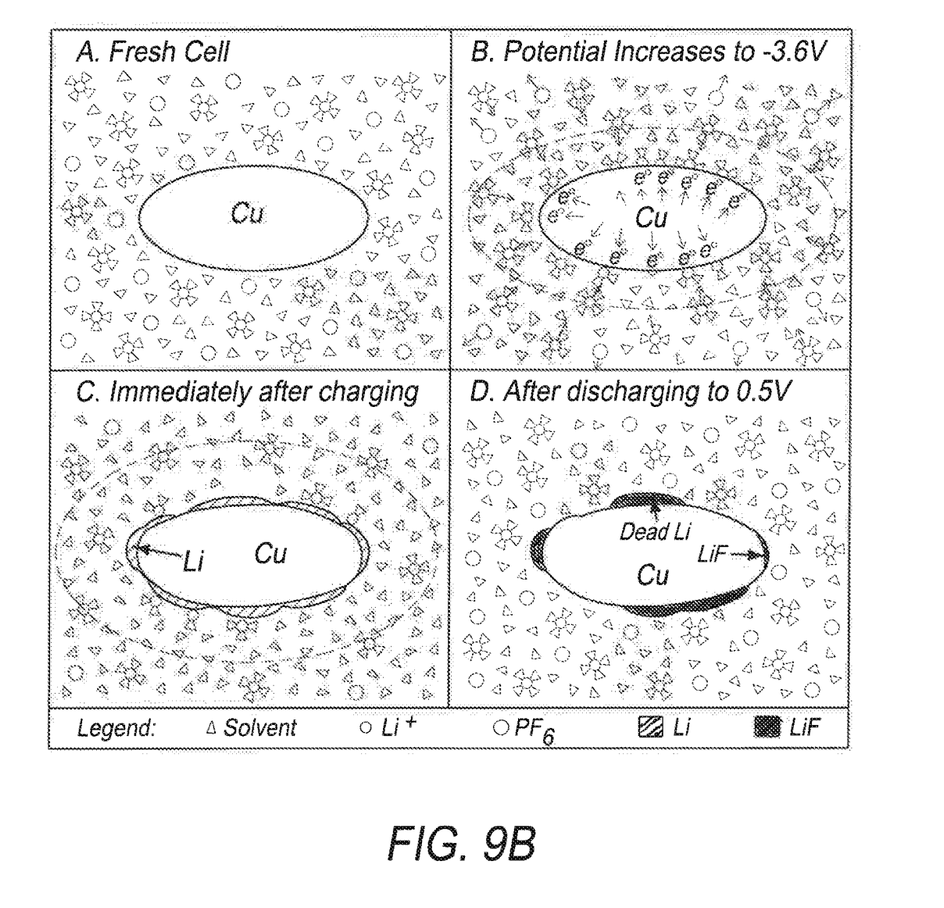

Referring next to FIGS. 9A-9B, a schematic illustration showing the molecular level stripping and clustering during the charge and discharge of a Li-ion battery. The top panel, FIG. 9A, shows the chare-discharge curves and the corresponding molecular migration is illustrated in A-D (FIG. 9B). (A) At the fresh cell State, $PF_6^-$ and solvated $Li^+$ ion are evenly distributed in the electrolyte. (B) When a potential is applied on the anode Cu nanoparticles, the $PF_6^-$ ions are repelled from the electrolyte around the Cu nanoparticles. When the potential increases to around 3.6V, solvated $Li^+$ ions start to lose solvent molecules and are reduced to metallic Li. (C) Immediately after charging, a layer of metallic Li forms on the Cu surface, while a solvent layer with a low concentration of $Li^+$ and depletion of $PF_6^-$ forms around the Cu nanoparticle. (D) After discharging partial of metallic Li was stripped back into electrolyte; however, some cannot be stripped because of the formation of an inert Li salt layer on top of the metallic Li.

While preferred embodiments of the present disclosure have been shown and described, it will be apparent to those of ordinary skill in the art that many changes and modifications may be made without departing from the disclosure in its true scope and broader aspects. Appended claims are therefore intended to cover all such changes and modifications as fall within the spirit and scope of the present disclosure.

The invention claimed is:

1. A method for in situ battery electrode analysis comprising:
   providing a battery cell having an anode and a cathode, as well as a ion permeable member having an opening;
   exposing the battery cell to an ion beam through the opening while the battery cell is operational to form secondary ions; and
   detecting the secondary ions to analyze the battery.

2. The method of claim 1 further comprising exposing the anode to the ion beam while the battery cell is operational to form the secondary ions.

3. The method of claim 1 further comprising exposing the electrolyte to the ion beam while the battery cell is operational to form the secondary ions.

4. The method of claim 1 further comprising determining the composition of the anode of the cell during charging or discharging of the cell.

5. The method of claim 1 further comprising determining the composition of the anode/electrolyte interface during the charging or discharging of the cell.

6. The method of claim 1 further comprising determining the composition of the cathode during charging or discharging of the cell.

7. The method of claim 1 further comprising determining the composition of the cathode/electrolyte interface during the charging or discharging of the cell.

8. The method of claim 1 further comprising determining the composition of the electrolyte during the charging or discharging of the cell.

9. The method of claim 1 wherein Li metal is deposited on the anode surface during charging and Li metal is stripped from the anode surface during discharging.

* * * * *

UNITED STATES PATENT AND TRADEMARK OFFICE
CERTIFICATE OF CORRECTION

PATENT NO. : 10,505,234 B2
APPLICATION NO. : 15/240937
DATED : December 10, 2019
INVENTOR(S) : Zihua Zhu and Chongmin Wang It is certified that error appears in the above-identified patent and that said Letters Patent is hereby corrected as shown below:

On the Title Page

(54) Title and in the Specification, 1st column 1, 1st line:
Replace "Battery Cell and n Situ Battery Electrode Analysis Method"
With --Battery Cell and In Situ Battery Electrode Analysis Method--

(56) References Cited, page 2, 1st column, 51st line:
Replace "WO 2016/088710 5/2018"
With --WO 2016/068710 5/2016--

(56) References Cited, page 2, 1st column, 57th line:
Replace "WO PCT/US2018/028708 Search Rept., dated Oct. 15, 2018"
With --WO PCT/US2018/026708 Search Rept., dated Oct. 15, 2018--

(56) References Cited, page 2, 1st column, 59th line:
Replace "WO PCT/US2018/028708 Writ. Opin., dated Oct. 15, 2018"
With --WO PCT/US2018/026708 Writ. Opin., dated Oct. 15, 2018--

(56) References Cited, page 2, 2nd column, 22nd line:
Replace "consiant in an electrochemical quartz crystal microbalance and the"
With --constant in an electrochemical quartz crystal microbalance and the--

(56) References Cited, page 2, 2nd column, 33rd line:
Replace "(ECRBS), Electrochimica Acta, 54, 20009, 1777-1783."
With --(ECRBS), Electrochimica Acta, 54, 2009, 1777-1783.--

(56) References Cited, page 2, 2nd column, 66th line:
Replace "Eiectrochimica Acta, 40, 10, 1995, 1249-1257."
With --Electrochimica Acta, 40, 10, 1995, 1249-1257.--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

(56) References Cited, page 3, 2nd column, 4th line:
Replace "Warrens, S., et al., X-ray structural analysis of semi-conductor-"
With --Warren, S., et al., X-ray structural analysis of semi-conductor- --

(56) References Cited, page 3, 2nd column, 5th line:
Replace "electrolyte interfaces, Workd Scientific Publ Co Pte Ltd, Singapore,"
With --electrolyte interfaces, World Scientific Publ Co Pte Ltd, Singapore,--

(56) References Cited, page 3, 2nd column, 14th line:
Replace "for in situ imaging by vacuum-based techiques, Journal of Vacuum"
With --for in situ imaging by vacuum-based techniques, Journal of Vacuum--

(56) References Cited, page 3, 2nd column, 17th line:
Replace "ToF-SIMS analysis of selected organic molecules at aqueous surfacesl"
With --ToF-SIMS analysis of selected organic molecules at aqueous surfaces--

(56) References Cited, page 3, 2nd column, 21st line:
Replace "Yu, X-Y., et al., Probing Aqueous Sruffaces by TOF-SIMS, Current"
With --Yu, X-Y., et al., Probing Aqueous Surfaces by TOF-SIMS, Current--

(56) References Cited, page 3, 2nd column, 27th line:
Replace "microfluidic rector by ToF-SIMS, Analyst, 139, 2014, 1609-1613."
With --microfluidic reactor by ToF-SIMS, Analyst, 139, 2014, 1609-1613.--

(56) References Cited, page 3, 2nd column, 34th line:
Replace "gold nanoperticles at aqueous surfaces, Sun Interface Anal., 46,"
With --gold nanoparticles at aqueous surfaces, Sun Interface Anal., 46,--

(56) References Cited, page 3, 2nd column, 36th line:
Replace "Yu, X-Y., et al., Imaging liquidsusing microfluidic calls, Microfluid"
With --Yu, X-Y., et al., Imaging liquids using microfluidic cells, Microfluid--

In the Drawings

Drawing Sheet 4 of 9, FIG. 4:
Replace "0~-4V CV scan, scna rate 10 mV/s"
With --0~-4V CV scan, scan rate 10 mV/s"--

In the Specification

Column 2, Line 43:
Replace "morphorlogy"
With --morphology--

CERTIFICATE OF CORRECTION (continued)
U.S. Pat. No. 10,505,234 B2

Column 9, Line 55:
Replace "chare-discharge"
With --charge-discharge--